United States Patent [19]

Kajander et al.

[11] Patent Number: 5,091,240

[45] Date of Patent: Feb. 25, 1992

[54] LAMINATE INCORPORATING HOT MELT AND WATER BASED ADHESIVES

[75] Inventors: Richard E. Kajander, Ware; David J. Fitzgerald, South Hadley, both of Mass.

[73] Assignee: Tambrands, Inc., Palmer, Mass.

[21] Appl. No.: 417,831

[22] Filed: Oct. 6, 1989

Related U.S. Application Data

[63] Continuation-in-part of Ser. No. 403,590, Sep. 5, 1989, abandoned.

[51] Int. Cl.$^5$ .............................................. B32B 9/00
[52] U.S. Cl. .................................. 428/198; 428/40; 428/284; 604/365; 604/366; 604/375
[58] Field of Search ............... 604/365, 366, 369, 375, 604/377, 382, 389, 393, 365; 428/198, 284, 40

[56] References Cited

U.S. PATENT DOCUMENTS

| | | | |
|---|---|---|---|
| 3,431,911 | 6/1966 | Meisel, Jr. | 128/287 |
| 3,461,872 | 5/1966 | McConnell et al. | 128/287 |
| 3,916,900 | 11/1975 | Breyer et al. | 128/287 |
| 4,287,251 | 8/1981 | King et al. | 428/198 |
| 4,718,898 | 1/1988 | Puletti et al. | 604/366 |
| 4,731,066 | 3/1988 | Korpman | 604/366 |
| 4,844,965 | 7/1989 | Foxman | 428/198 |
| 4,872,870 | 10/1989 | Jackson | 604/366 |
| 4,904,249 | 2/1990 | Miller et al. | 428/284 |
| 4,961,982 | 10/1990 | Taylor | 428/284 |

Primary Examiner—Patrick J. Ryan
Assistant Examiner—Elizabeth Evans
Attorney, Agent, or Firm—Fish & Richardson

[57] ABSTRACT

A combination of hot melt and water-based adhesives (solution resin or latex) is particularly advantageous for bonding fibers together to form a layer and for bonding that layer to an adjoining layer. The water-based adhesive, which need not be crosslinkable, provides fiber-to-fiber bonding through the layer of fibers, while the hot melt adhesive bonds the layer of fibers to the adjoining layer. In preferred embodiments, the layer of fibers is moisture absorbent and formed of wood pulp, cotton, rayon, or cellulose triacetate fibers (possibly with the addition of a small amount of thermoplastic fibers to increase bulk); the fibers can be reprocessed fibers of irregular lengths; the water-based adhesive is a latex, non-crosslinkable adhesive; the adjoining layer is permeable to moisture and made of a nonwoven polyolefin, rayon, polyester, or blend thereof; a moisture-barrier layer (e.g., closed-cell foam or moisture-impervious film) is adhered by hot melt adhesive to the other surface of the layer of fibers; the laminate forms a panty shield.

21 Claims, 2 Drawing Sheets

LAMINATE INCORPORATING HOT MELT AND WATER BASED ADHESIVES

This application is a continuation in part of our pending application entitled "Laminate Incorporating Hot Melt and Water Based Adhesives" filed on Sept. 5, 1989 Ser. No. 07/403,590 now abandoned.

BACKGROUND OF THE INVENTION

This invention relates to laminates incorporating a fibrous layer, and particularly to disposable absorbent products such as panty shields, sanitary napkins, diapers, absorbent towels, and bed liners.

Panty shields consist essentially of three layers: a permeable layer through which liquid passes, a layer of fibers for absorbing the liquid, and a moisture-barrier layer beneath the fibers. Some means must be provided for holding the fibers together to form a layer so that the laminate does not fall apart, and the layer of fibers must be bonded to the adjoining layers.

Several approaches have been taken in the prior art. One common technique is to seal the fibers within an envelope formed by sealing the permeable and barrier layers together at their perimeters. These layers are typically thermoplastic, and are bonded to each other by application of heat (or with adhesive).

Another approach has been to add thermoplastic powders, fibers, or fibrils to the fibrous layer and to apply heat during lamination to form a supporting web of thermoplastic material throughout the fibrous layer as well as a bond between the thermoplastic web and adjoining, thermoplastic permeable and barrier layers. Typically, the laminate is embossed during application of heat so that bonding occurs primarily in embossed areas.

Crosslinkable latex adhesives have also been employed. The layer of fibers is impregnated with such adhesives during lamination, and the laminate is then cured in drying ovens to form bonds between fibers as well as between the layer of fibers and the adjoining permeable and barrier layers. This is commonly done stepwise in separate operations. Embossing has also been used in such constructions to cause the latex adhesive to migrate into the embossed areas prior to curing.

Absorbent fibrous webs have also been made on specialized equipment that consolidates loose fibers using such techniques as spunlacing, mercerizing, or needle punching to mechanically entangle the fibers into a web. Uniform fibers are generally required, and the mechanical entanglement step must be done off-line (i.e., in a separate manufacturing process not part of the process for assembling the panty shield or other disposable absorbent article).

Hot melt adhesives have been used in the manufacture of laminates. A known technique for applying such adhesives is to apply a coating of the adhesive to one or more layers prior to forming the laminate.

SUMMARY OF THE INVENTION

We have found that a combination of hot melt and water-based adhesives (solution resin or latex) is particularly advantageous for bonding fibers together to form a layer and for bonding that layer to an adjoining layer. The water-based adhesive, which need not be crosslinkable, provides fiber-to-fiber bonding through the layer of fibers, while the hot melt adhesive bonds the layer of fibers to the adjoining layer.

In preferred embodiments, the layer of fibers is moisture absorbent and formed of wood pulp, cotton, rayon, or cellulose triacetate fibers (possibly with the addition of a small amount of thermoplastic fibers to increase bulk); the fibers can be reprocessed fibers of irregular lengths; the water-based adhesive is a latex, non-crosslinkable adhesive; the adjoining layer is permeable to moisture and made of a nonwoven polyolefin, rayon, polyester, or blend thereof; a moisture-barrier layer (e.g., closed-cell foam or moisture-impervious film) is adhered by hot melt adhesive to the other surface of the layer of fibers; the laminate forms a panty shield; the moisture permeable layer is between 0.25 and 2.00 oz./yd$^2$; between 0.1 and 0.75 mg/cm$^2$ of hot melt adhesive is used to bond the permeable layer to the layer of fibers; between 0.2 and 2.5 mg/cm$^2$ of water-based adhesive is applied to the fibers; between 50 and 300 mg/cm$^2$ of fibers are used to form the layer of fibers; the closed cell foam is between 15 and 63 mils thick; between 0.8 and 2.0 mg/cm$^2$ of hot melt adhesive is used to bond the layer of fibers to the layer of closed cell foam; the water-based adhesive migrates into densified regions in the layer of fibers; the densified regions are formed by embossing; the edge of the laminate is densified during die cutting, with resulting migration of water-based adhesive; the migration of adhesive to the edge of the layer of fibers tends to reduce fiber loss at the edge.

In a second aspect, the invention features a method for manufacturing a laminate having a layer of fibers adhered to an adjoining layer. Regions of the layer of fibers are impregnated with a water-based adhesive to provide fiber-to-fiber bonds through the layer; hot melt adhesive is applied either to the adhesive-impregnated layer of fibers or to the adjoining layer; and the layer of fibers and adjoining layer are adhered. In preferred embodiments, the adhering step is performed before the water-based adhesive has dried; the adhesives are applied by spraying; the resulting laminate is die cut into pieces (e.g., panty shields) and the pieces are packaged all before the water-based adhesive has dried.

In a third aspect, the invention features a panty shield in which a foam layer extends to the edge of the shield to provide a softer edge. In preferred embodiments, the layer of fibers also extends to the edge of the product; the foam layer is from 0.015 to 0.063 inches thick (most probably 0.025 to 0.035 inches).

The invention provides a simpler and less expensive method of manufacturing laminates with fibrous layers. It allows the use of almost any type of fiber, including reprocessed fibers of irregular length, as well as very short fibers (e.g., wood pulp), without leakage of loose fibers at the edges of the product. Small amounts (e.g., up to 10% by weight) of thermoplastic fibers can be added to increase the bulk of the fibrous layer. By making possible the use of non-crosslinking water-based adhesives, the invention improves manufacturing safety, as uncured crosslinkable water-based adhesives tend to be more irritating to skin than those that are non-crosslinking. The manufacturing process is also simplified by the use of non-crosslinking water-based adhesives, because curing ovens are eliminated and there is no longer a need to perform the die cutting operation in a second, off-line procedure following adhesive drying.

The invention also provides an improved panty shield. The exposed fiber layer at the edge of the product provides a softer edge, as does the use of a foam layer extending to the edge.

DESCRIPTION OF THE PREFERRED EMBODIMENT

Figure 1:
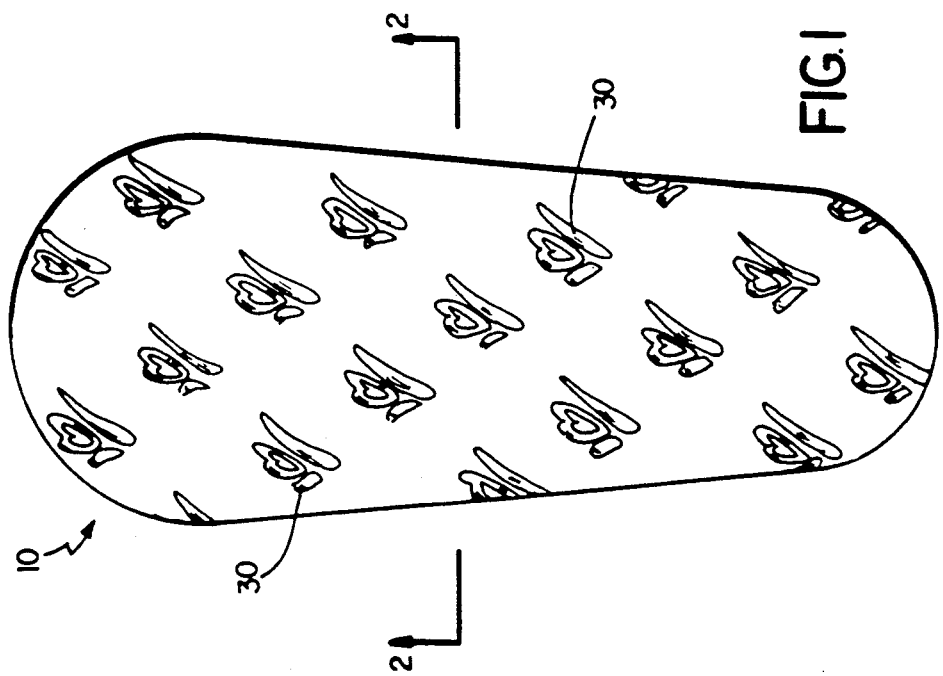
FIG. 1 is a plan view of a preferred panty shield embodiment of the invention.
Figure 2:
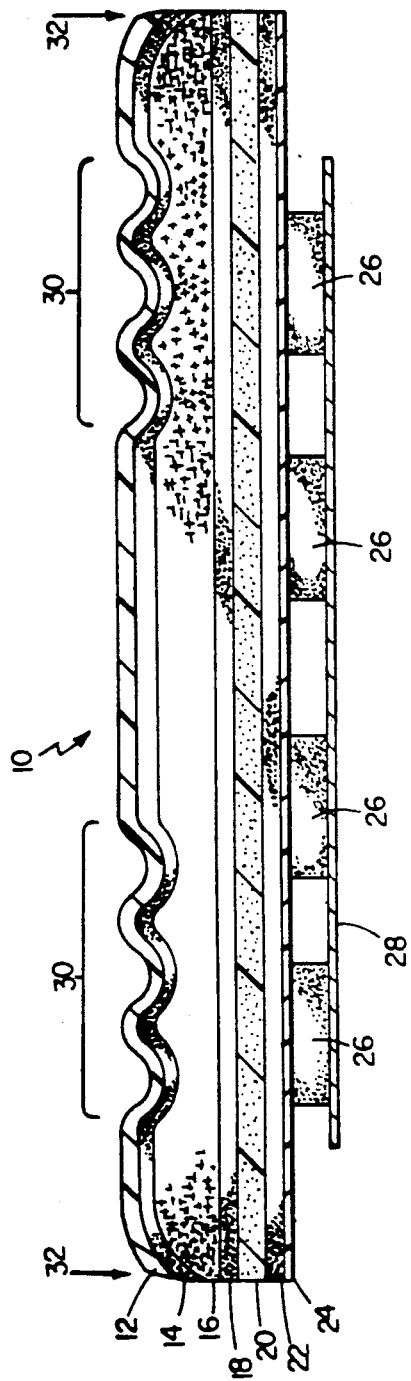
FIG. 2 is a cross-sectional, diagrammatic view at 2—2 of FIG. 1 (vertical dimension exaggerated).

Shown in FIGS. 1 and 2 is a panty shield 10 having a permeable top sheet 12 (nonwoven polypropylene, 0.5 oz/yd$^2$), layer 14 of hot melt adhesive (spray applied, 0.47 mg/c$^2$), layer 16 of fibers impregnated with latex adhesive, layer 18 of hot melt adhesive (spray applied, 141 mg/cm$^2$), foam layer 20 (1/32 inch closed-cell polyethylene), layer 22 of hot melt adhesive (spray applied, 141 mg/cm$^2$), back sheet 24 (nonwoven polypropylene, 0.5 oz/yd$^2$), pressure-sensitive adhesive stripes 26 (block copolymer rubber adhesive), and release liner 28 (silicone coated paper).

The hot melt adhesive used in layers 14, 18, 22 has cold tack to improve its adherence to the latex-moistened fiber core, and the adhesive is spray applied in a uniform pattern, atomized with heated air into very small spherical or fiber-like particles. Suitable hot melt adhesives are Findley 593-335, an ethylene vinyl acetate blend, and Findley 582-371, as well as various amorphous polypropylenes, all available from Findley, of Milwaukee, Wis. Practical ranges on the amounts of hot melt adhesive to be applied to the various layers are 0.1–0.75 mg/cm$^2$ for adhesive layer 14 and 0.8–2.0 mg/cm$^2$ for layers 18, 22.

A wide variety of fibers can be used in the fiber core 16, including blends of reprocessed, clean rayon and cotton fibers of irregular length. Virgin fibers such as wood pulp, cotton, staple-cut rayon or cellulose triacetate can also be used with equally good results. Preferably, the fibers have lengths in the range 0.05 to 2.0 inches, and 50 to 300 gm/m$^2$ of fibers are used to form layer 16.

The latex adhesive is uniformly applied to fiber layer 16 by spraying, but it tends to migrate into densified areas prior to drying. This migration is primarily to embossed areas 30. But some migration to the peripheral edge 32 occurs, where the adhesive aids in resisting fiber loss from the exposed edges of the layer of fibers. The preferred latex is a non-crosslinking type, such as PD-0120, a vinyl acrylic, available from H.B. Fuller, of Minneapolis, Minn. (an alternative is PD-062, also available from H.B. Fuller). The latex is spray applied to the fiber core at a rate of 0.2–2.5 mg/cm$^2$ (most preferably 0.5–1.0 mg/cm$^2$) solids. The preferred PD-0120 latex has 55% solids, but greater or lesser concentrations of solids can be used. The latex is dried under ambient conditions, and it may take two days or more for full drying to occur. But even while the latex is wet, it provides sufficient integrity to the laminate to permit the laminate to be fully assembled and cut, and the resulting panty shields packaged for shipment.

Foam layer 20 serves as a moisture barrier and as a means for softening the edge of the product, to make it more comfortable to the user. A wide variety of foam materials can be used, but it is preferred that the foam be closed cell, so that it serves as a moisture barrier. Back sheet 24 provides improved appearance and feel to the product, but is otherwise nonfunctional.

Figure 3:
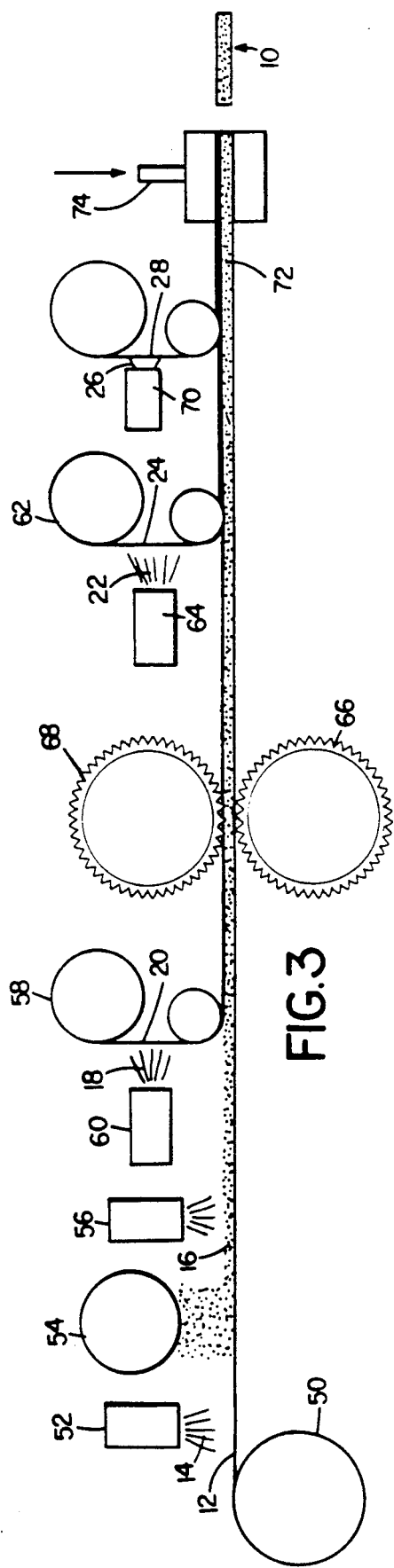
FIG. 3 is a diagrammatic view of the manufacturing process used in making the panty shield.

The manufacturing process used to make the product of FIGS. 1 and 2 is shown diagrammatically in FIG. 3. Top sheet 12 unwinding from roll 50 is sprayed with hot melt adhesive 14 from sprayer 52. Garnet wheel 54 deposits loose fibers over the sprayed hot melt, and latex is sprayed over the loose fibers by sprayer 56. Foam layer 20 unwinding from roll 58 and sprayed with hot melt adhesive 18 from sprayer 60 is applied to the latex-moistened fibers. Back sheet 24 unwinding from roll 62 is sprayed with hot melt adhesive 22 from sprayer 64 and applied to foam layer 20 after embossing by embossing wheels 66, 68. Release liner 28, to which pressure-sensitive adhesive 26 has been applied by applicator 70, is applied to the back sheet. Finally, the finished laminate 72 is cut into the desired panty shields 10 using die 74. The shields are then immediately packaged for shipment, well prior to full drying of the latex adhesive impregnating the fibers.

During the embossing and cutting steps, the latex adhesive begins to wick into the resulting densified regions in the fiber layer. Although latex remains on the back surface of fibrous layer 16, where it was sprayed, migration into the core of the fibrous layer occurs primarily in the densified regions. There is very little latex migration into the undensified areas. The latex can take anywhere from an hour to five days to fully dry, depending on the packaging, initial moisture levels of the loose fibers, and the amount of adhesive used.

Unlike the latex, which migrates through the fibers in the densified areas, the hot melt adhesive applied to each side of the fiber layer does not migrate. Thus, while the hot melt adhesive is only able to adhere to fibers along the surfaces of fibrous layer 16, the latex adhesive provides fiber-to-fiber bonding through the fibrous layer, to hold the layer together.

The hot melt adhesive is able to successfully bond the fibrous layer 16 to adjoining layers 12 and 20, despite the fact that the latex adhesive in the fibrous layer has not even begun to dry at the time that the hot melt adhesive is applied between the layers. This result is particularly surprising in the case of the bond between foam layer 20 and the fibrous layer 16, as the hot melt adhesive first contacts the fibers after they have been moistened with the latex adhesive.

The edge of the panty shield is softened and made more comfortable for the user by the use of foam layer 20 and by the exposed fibers at the edge of the laminate (as contrast with a sealed-edge construction in which top and bottom layers of the laminate extend beyond the fibers, creating a thinner, stiffer, and thus less comfortable edge).

OTHER EMBODIMENTS

Other embodiments of the invention are within the following claims. For example, a wide variety of absorbent products in which a fiber core is bonded to an adjoining layer can incorporate the invention, including baby diapers, adult diapers, wound dressings, and absorbent towels. In some of these products (e.g., towels), the fiber core is sandwiched between two permeable layers, so that liquid can enter from either side.

In the panty shield embodiment described herein, wide variations in construction are possible. For example, variations can be made in the type of layers, the materials used in the layers, the dimensions of the layers, and the amounts of adhesives used. One variation would be to use a single, impermeable thermoplastic film to replace foam layer 20, hot-melt layer 22, and back sheet 24. Nonwoven, permeable layer 12 can vary in weight, but is preferably between 0.25 and 2.00 oz/yd$^2$. Similarly, foam layer 20 can vary in thickness, but is preferably between 15 and 63 mils. An alternative to a foam layer is a layer of soft film (e.g., polyolefin or copolymers, 0.5 to 2.5 mils thick). The hot melt adhesive could be applied by printing or scraping, and it could be applied directly over the latex-moistened fibers instead of first to another layer.

Figure 5:
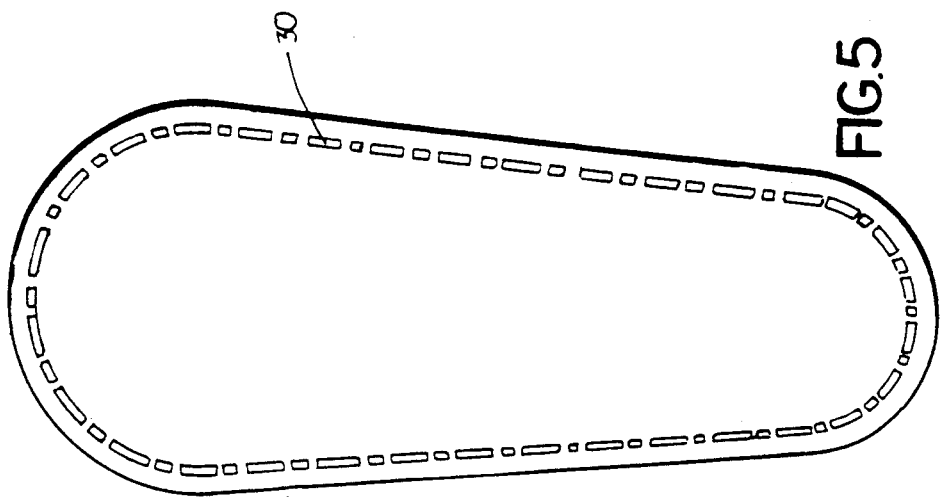
FIGS. 4 and 5 are plan views of alternative panty shield embodiments.
Figure 4:
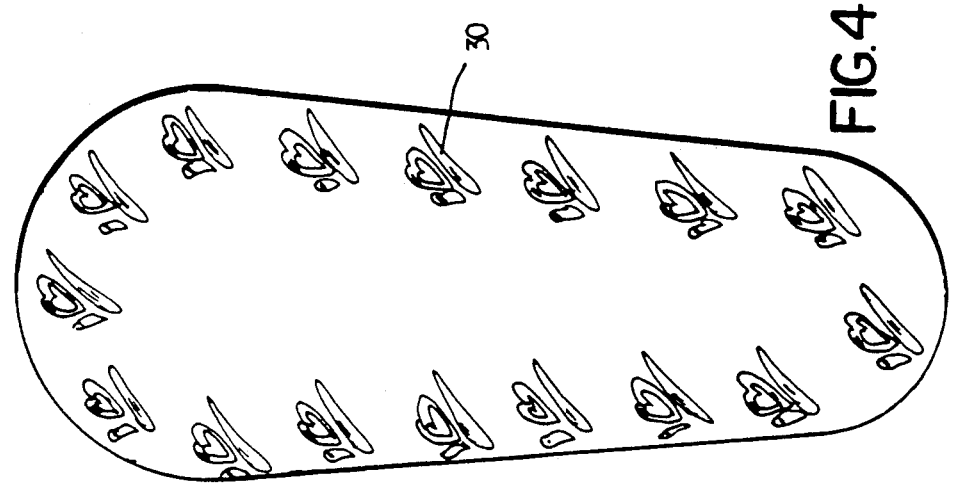

Two further variations in the panty shield embodiment are shown in FIGS. 4 and 5, wherein the over-all embossed pattern is replaced with a perimeter pattern, in registration with the die-cut edge, consisting either of the same decorative figures used in the over-all pattern (FIG. 4) or a simple dashed line 130 (FIG. 5). A solid line could replace the dashed line, and either the solid or dashed line could be combined with an over-all embossed pattern.

We claim:

1. A laminate comprising
   fibers held together in a moisture absorbent layer by water-based adhesive polymer that impregnates at least some regions of said layer and in those regions provides fiber-to-fiber bonding through said layer,
   a layer of hot melt adhesives; and
   a layer of hot melt adhered to said layer of fibers by said hot melt adhesive, said hot melt adhesive providing bonding between said moisture absorbent layer and said adjoining layer.

2. The laminate of claim 1 wherein said layer of fibers comprises fibers from the group consisting of wood pulp, cotton, rayon, and cellulose triacetate.

3. The laminate of claim 2 wherein said layer of fibers further comprises up to 10% by weight thermoplastic fibers.

4. The laminate of claim 2 wherein said fibers are reprocessed fibers of irregular lengths.

5. The laminate of claim 1 wherein said water-based adhesive polymer is a non-crosslinkable latex adhesive.

6. The laminate of claim 5 wherein the bond between said layer of fibers and said adjoining layer is provided by said hot melt adhesive and the fiber-to-fiber bond within said layer of fibers is provided by said water-based adhesive.

7. The laminate of claim 5 wherein said adjoining layer is permeable to moisture.

8. The laminate of claim 7 wherein said permeable material is nonwoven.

9. The laminate of claim 7 wherein said adjoining layer comprises material selected from the group consisting of nonwoven polyolefin, rayon, polyester, and blends of said materials.

10. The laminate of claim 7 wherein said layer of fibers is adhered to a second, adjoining layer on its other surface, said second layer being a moisture barrier, and wherein said moisture-barrier layer is adhered to said layer of fibers by hot melt adhesive.

11. The laminate of claim 10 wherein said laminate forms a panty shield.

12. The laminate of claim 11 wherein said moisture barrier comprises a layer of closed cell foam.

13. The laminate of claim 12 wherein
    said water-based adhesive is a latex adhesive,
    said permeable layer is between 0.25 and 2.00 oz/yd$^2$ in weight
    between 0.1 and 0.75 mg/cm$^2$ of hot melt adhesive is used to bond said permeable layer to said layer of fibers,
    between 0.2 and 2.5 mg/cm$^2$ of water-based adhesive is applied to said fibers,
    between 50 and 300 gm/m$^2$ of fibers are used to form said layer of fibers,
    said layer of closed cell foam is between 15 and 63 mils thick, and
    between 0.8 and 2.0 mg/cm$^2$ used to bond said layer of fibers to said layer of closed cell foam.

14. The laminate of claim 11 further comprising adhesive means for adhering said shield to a panty.

15. The laminate of claims 1 or 11 wherein said layer of fibers has densified regions into which said water-based adhesive has migrated before drying.

16. The laminate of claim 15 wherein densified regions are formed by embossing said laminate before said water-based adhesive has dried.

17. The laminate of claim 16 wherein said layer of fibers are exposed at the edge of said laminate, and wherein said fibers are densified at said edge with resulting migration of water-based adhesive to said edge.

18. The laminate of claim 17 wherein said migration of water-based adhesive to said edge results in adhesive being present to reduce fiber loss at said edge by comparison to the loss occurring without said migration of adhesive.

19. The laminate of claim 18 wherein said migration of water-based adhesive to said edge is the consequence of die cutting said edge.

20. The laminate of claim 1 or 11 wherein hot melt adhesive adheres said layer of fibers to each said adjoining layer.

21. The laminate of claim 20 wherein the hot melt adhesive is uniformly distributed across the interface between said layer of fibers and each said adjoining layer.

* * * * *

UNITED STATES PATENT AND TRADEMARK OFFICE
CERTIFICATE OF CORRECTION

PATENT NO.  : 5,091,240
DATED       : 2/25/92
INVENTOR(S) : Richard E. Kajander and David J. Fitzgerald It is certified that error appears in the above-identified patent and that said Letters Patent is hereby corrected as shown below:

Column 3, line 17, "$c^2$" should be --$cm^2$--.

Column 5, line 28, "adhesives" should be --adhesive--.

Column 5, line 29, "a layer of hot melt" should be replaced with --an adjoining layer--.

Column 6, line 25, before "used", insert --of hot melt adhesive is--.

Signed and Sealed this

Eighth Day of June, 1993

Attest:

MICHAEL K. KIRK

*Attesting Officer*       *Acting Commissioner of Patents and Trademarks*